United States Patent [19]

Pang

[11] Patent Number: 5,418,135
[45] Date of Patent: May 23, 1995

[54] METHOD OF INHIBITING BINDING OF PDGF TO A PDGF RECEPTOR BY BIOSYNTHETIC PDGF ANTAGONISTS

[75] Inventor: Roy H. L. Pang, Medway, Mass.

[73] Assignee: Creative BioMolecules, Inc., Hopkinton, Mass.

[21] Appl. No.: 95,898

[22] Filed: Jul. 21, 1993

Related U.S. Application Data

[63] Continuation of Ser. No. 632,068, Dec. 21, 1990, abandoned.

[51] Int. Cl.6 ............ C12Q 1/00; G01N 33/53; A61K 37/02; C07K 5/00
[52] U.S. Cl. ............ 435/7.1; 435/7.2; 435/7.2 W; 435/7.32; 435/240.2; 424/143.1; 530/324; 530/350; 530/399
[58] Field of Search ............ 530/324, 350, 399, 329, 530/330; 514/12, 970; 435/69.4, 7.1, 7.2, 240.2, 320.1; 536/7.21, 7.32, 23.1, 23.51; 424/143.1

[56] References Cited

U.S. PATENT DOCUMENTS 5,128,321  7/1992  Murray et al. .................. 514/12

OTHER PUBLICATIONS

Antoniades et al., Proc. Natl. Acad. Sci. USA, 76:1809–1813 (1979).
Barrett et al., Proc. Natl. Acad. Sci. USA, 85:2810–2814 (1988).
Betsholtz et al., Nature, 320:695–699 (1986).
Bonthron et al., Proc. Natl. Acad. Sci. USA, 85:1492–1496 (1988).
Friedman et al., J. Clin. Invest., 60:1191–1201 (1977).
Geise et al., Mol. and Cell. Biol., 10:5496–5501 (1990).
Heldin et al., Proc. Natl. Acad. Sci. USA, 76:3722–3726 (1979).
Hoppe et al., Biochem., 28:2956–2960 (1989).
Hosang, J. Cell. Physiol., 134:396–404 (1988).
Hosang, et al., J. Cell. Biochem., 29:265–273 (1985).
Huang, J. Cell. Biochem., 26:205–220 (1984).
Johnsson et al., Embo J., 3:921–928 (1984).
Kawahara et al., Biochem. Biophys. Res. Commun., 147:839–845 (1987).
Kloer, Am. J. Med., 83:3–8 (1987).
Lockridge et al., J. Biol. Chem., 262:12945–12952 (1987).
Messing et al., Nucleic Acids Res., 9:309–321 (1981).
Mordan, L. J., Cancer Research, 49:906–909 (1989).
Ohnishi et al., Life Sciences, 31:2595–2602 (1982).
Rutherford et al., J. Cell. Biol., 69:196–203 (1976).
Sanger et al., J. Mol. Biol., 94:441–448 (1975).
Tiell et al., Artery, 12:33–50 (1983).
Tong et al., Nature, 328:619–621 (1987).
Welinder, K. G., Anal. Biochem., 174:54–64 (1988).
Zagari, et al., Biochem. Biophys. Res. Commun., 150:1207–1212 (1988).

Primary Examiner—Garnette D. Draper
Assistant Examiner—Gian P. Wang
Attorney, Agent, or Firm—Testa, Hurwitz & Thibeault

[57] ABSTRACT

Disclosed are polypeptides which antagonize the activity of platelet-derived growth factor (PDGF). These polypeptides include an amino acid sequence sufficiently duplicative of at least a portion of the amino acid sequence of an A chain of PDGF such that the polypeptides bind a cell membrane-bound receptor for native PDGF on a cell that responds biologically to the binding of PDGF. The binding of the antagonist to the receptor is effective to inhibit PDGF binding and activity. Also disclosed are methods of preparing and using these antagonists.

9 Claims, 6 Drawing Sheets

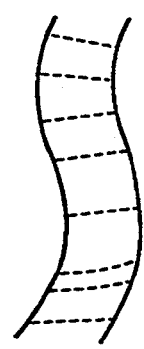
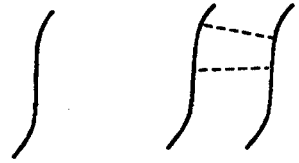
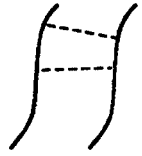
Fig. 1A    Fig. 1B    Fig. 1C    Fig. 1D
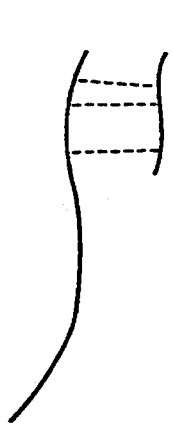
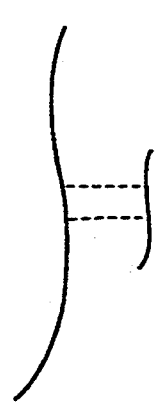
Fig. 1E    Fig. 1F    Fig. 1G

FIGURE 2

```
         10         20         30         40         50
GAATTCATGTCTATCGAAGAAGCGGTACCGGCTGTTTGTAAAACTCGTAC
     M  S  I  E  E  A  V  P  A  V  C  K  T  R  T
EcoRINlaIII    MboII+   BanIHpaII              RsaI
          TaqI      KpnI
                    NlaIV
                    RsaI 60         70         80         90        100
TGTTATCTACGAAATCCCGAGATCTCAGGTTGACCCGACGTCTGCTAACT
  V  I  Y  E  I  P  R  S  Q  V  D  P  T  S  A  N  F
          AvaIBglII     HincII   AatII
                  DdeI           AhaII
               Sau3A
               XhoII 110        120        130        140        150
TCCTGATCTGGCCACCGTGTGTTGAAGTTAAACGTTGTACTGGTTGTTGT
   L  I  W  P  P  C  V  E  V  K  R  C  T  G  C  C
       BalIDraIII                 RsaI
   Sau3AHaeIII
       CfrI 160        170        180        190        200
AACACCTCGAGCGTTAAATGTCAGCCGTCTCGTGTTCACCATCGATCTGT
  N  T  S  S  V  K  C  Q  P  S  R  V  H  H  R  S  V
   AvaI                              HphI-ClaI
   MnlI+                                  Sau3A
    TaqI                                  TaqI
    XhoI 210        220        230        240        250
TAAAGTCGCGAAAGTTGAATACGTTCGTAAGAAACCGAAACTTAAGGAAG
   K  V  A  K  V  E  Y  V  R  K  K  P  K  L  K  E  V
     FnuDII    XmnI                       AflII
     NruI 260        270        280        290        300
TTCAGGTTCGTCTGGAAGAACACCTGGAATGTGCATGCGCTACTACAAGC
     Q  V  R  L  E  E  H  L  E  C  A  C  A  T  T  S
            MboII+  EcoRII       SphIHhaI        Alu
                    ScrFI           HinPI        Hind
                                    NlaIII
                                    NspHI
```

FIGURE 2, conti'.

```
     310       320       330       340          350
TTGAATCCGGACTACCGTGAGGAGGACACTGACGTCCGTTAA
 L   N   P   D   Y   R   E   E   D   T   D   V   R   *
 I     BspMII         MnlI-             AccI
III    HpaII          MnlI-
   HinfI
```

Underscored amino acid sequence is that of an A chain of PDGF.

* signifies the end of the structural gene encoding the A chain.

FIGURE 3

```
         10        20        30        40        50
GAATTCATGTCTATCGAAGAAGCGGTACCGGCTGTTTGTAAAACTCGTAC
     M  S  I  E  E  A  V  P  A  V  C  K  T  R  T
EcoRINlaIII    MboII+   BanIHpaII                RsaI
           TaqI         KpnI
                        NlaIV
                        RsaI 60        70        80        90       100
TGTTATCTACGAAATCCCGAGATCTCAGGTTGACCCGACGTCTGCTAACT
  V  I  Y  E  I  P  R  S  Q  V  D  P  T  S  A  N
              AvaIBglII      HincII  AatII
                   DdeI              AhaII
                 Sau3A
                 XhoII 110       120       130       140       150
TCCTGATCTGGCCACCGTGTGTTGAAGTTAAACGTTGTACTGGTTGTTGT
  F  L  I  W  P  P  C  V  E  V  K  R  C  T  G  C  C
       BalIDraIII                   RsaI
   Sau3AHaeIII
      CfrI 160       170       180       190       200
AACACCTCGAGCGTTAAATGTCAGCCGTCTCGTGTTCACCATCGATCTGT
  N  T  S  S  V  K  C  Q  P  S  R  V  H  H  R  S  V
     AvaI                           HphI-ClaI
     MnlI+                                  Sau3A
      TaqI                                   TaqI
      XhoI 210       220       230       240       250
TAAAGTCGCGAAAGTTGAATACGTTCGTAAGAAACCGAAACTTAAGGAAG
  K  V  A  K  V  E  Y  V  R  K  K  P  K  L  K  E  V
     FnuDII   XmnI                    AflII
     NruI
```

FIGURE 3, conti'.

```
      255         265         275         285         295
TTCAGGTTCGTCTGGAAGAACACCTGGAATGTGCATGCGCTACTACAAGC
  Q   V   R   L   E   E   H   L   E   C   A   C   A   T   T   S
            MboII+   EcoRII      SphIHhaI              Alu
                     ScrFI           HinPI             Hind
                                  NlaIII
                                  NspHI 310         320         330         340         350
TTGAATCCGGACTACCGTGAGGAGGACACTGGTAGACCGCGTGAATCTGG
  L   N   P   D   Y   R   E   E   D   T   G   R   P   R   E   S   G
I      BspMII           MnlI-        AccI   FnuDII
III    HpaII            MnlI-                   HinfI
  HinfI 360         370              385         395
405
TAAGAAACGTAAGCGTAAACGTCTGAAACCGACTTAAGGATCCGTCGACGTGCA
  K   K   R   K   R   K   R   L   K   P   T   *    G   S
(polylinker)                                  AflIIBamHI
                                                   NlaIV
                                                   Sau3A
                                                   XhoII
```

Underscored amino acid sequence is that of an A chain of PDGF.

* signifies the end of the structural gene encoding the A chain.

Underscored nucleic acid sequence is a portion of the polylinker.

FIGURE 4

```
        10        20        30        40        50
AATATTCTGAAATGAGCTGTTGACAATTAATCATCGAACTAGTTAACTAG
SspI
Trp-promoter/operator -->

60        70        80        90        100
TACGCAAGTTCTCGTAAAAAGGGTATCGACAATGAAAGCAATTTTCGTAC
                                M  K  A  I  F  V  L
                                : --> modified LE 110       120       130       140       150
TGAAAGGTTCACTGGACAGAGATCTGGACTCTCGTCTGGATCTGGACGTT
  K  G  S  L  D  R  D  L  D  S  R  L  D  L  D  V
leader peptide       BglII 160       170       180       190       200
CGTACCGACCACAAAGACCTGTCTGATCACCTGGTTCTGGTCGACCTGGC
  R  T  D  H  K  D  L  S  D  H  L  V  L  V  D  L  A 210       220       230       240       250
TCGTAACGACCTGGCTCGTATCGTTACTCCCGGGTCTCGTTACGTTGCGG
  R  N  D  L  A  R  I  V  T  P  G  S  R  Y  V  A  D 260
ATCTGGAATTCATG
   L  E  F  M
     EcoRI      : --> gene for PDGF
```

METHOD OF INHIBITING BINDING OF PDGF TO A PDGF RECEPTOR BY BIOSYNTHETIC PDGF ANTAGONISTS

This is a continuation of application Ser. No. 07/632,068 filed on Dec. 21, 1999, now abandoned.

BACKGROUND OF THE INVENTION

Atherosclerosis, a cardiovascular disease characterized by a thickening of the intima of muscular arteries, is the principal cause of myocardial and cerebral infarction, conditions which often ultimately result in death. The thickening occurs in large and mid-sized arteries, and may include fatty streaks, and later, in a markedly thickened layer that narrows the lumen of the vessel, resulting in clinical symptoms. The intimal thickening in advanced lesions or fibrous plaques includes a fibrotic layer of smooth muscle cells (SMC) and connective tissue matrix overlying a lipid-rich region beneath. The vessel becomes unstable under the stress of the high arterial flow rate as the lipid substructure is a weak supporting base. Additionally, accumulation of thrombotic material at the site of thickening may result in complete obstruction of the vessel lumen.

The etiology of atherosclerosis is unknown. However, it is hypothesized that an event which results in a change, injury, and/or disruption of the endothelial layer surrounding the lumen and overlying the SMC layer initiates the process. Upon sustaining the injury, a complex sequence of events is then initiated which leads to the ultimate formation of an atherosclerotic plaque. The endothelial cells becomes proliferative in an attempt to regenerate denuded regions of the lining of the vessel. Injury to endothelial linings is believed to cause circulating platelets to aggregate at the site of the injury where they adhere to exposed tissue at the wound site. Edema occurs at the site of injury, perhaps aiding the infiltration of macrophages which have migrated from blood and underlying tissue layers. These macrophages proliferate, and some ingest low density lipoproteins deposited at the site of injury, thereby becoming lipid-laden foam cells. The SMC at the site of the injury also change from a quiescent state to a synthetic state, proliferating and producing extracellular matrix materials such as collagen, elastin, and proteoglycans. A thickening extending into the lumen of the artery thus develops.

A high concentration of platelet-derived growth factor (PDGF) is found at the site of the lesion, and later, in the fibrous plaque (Barrett et al. (1988) Proc. Natl. Acad. Sci. 85:2810–2814). This growth factor is known to bind to receptors on the surface of various cells, thereby initiating a sequence of intracellular events that ultimately result in proliferation of those cells.

Native PDGF is a dimeric molecule consisting of two polypeptide chains, one or more of which appear to be glycosylated. The two chains (referred to as A or alpha and B or beta) are homologous but not identical. They have molecular weights of about 17,000 to 18,000 daltons and about 13,000 to 14,000 daltons, respectively. In vivo, the A and B chains are synthesized from larger precursors which are subsequently processed at the amino and carboxyl termini. The mature human A chain consists of 110 or 125 amino acids and various N-linked sugar side chains, the length and amino acid sequence being dependent on the tissue source. The fully processed human B chain is encoded by the C-sis gene and consists of 112 amino acids. It has been found to have a high degree of homology with the $p28^{sis}$ protein product of the v-sis transforming gene of simian sarcoma virus (SSV) (Johnsson et al., (1984) Embo. 3:921).

Biologically active PDGF can exist as an AA or BB homodimer, having a molecular weight of about 35,000 daltons (35 kD) or about 32 kD, respectively, or can take the form of an AB heterodimer having a molecular weight of about 34 kD. The human PDGF dimer is glycosylated and processed post-translationally into a three-dimensional conformation that is biologically active. This conformation is maintained by relatively weak noncovalent hydrogen bonds, hydrophobic and charge interactions, and strong covalent bonds between sulfur atoms in cysteine residues. The PDGF dimer has eight such disulfide linkages which exist both between chains (interchain bonds) and within the same chain (intrachain bonds). Reduction of either the AA or BB dimer into its component monomeric chains destroys all biological activity.

Different cell types are known to elicit different dimeric forms of PDGF. In fact, many of the cells intimately involved in the formation of the plaque produce and secrete various forms of PDGF. For example, platelets aggregating at the site of initial injury at the endothelial lining release PDGF AB. Macrophages produce PDGF BB, and SMC and endothelial cells produce PDGF AA.

Platelet-derived growth factor has been postulated to be the etiological agent in atherosclerosis (see e.g., Rutherford et al. (1976) J. Cell. Biol. 69:196–203; Friedman et al. (1977) J. Clin. Invest. 60:1191–1201). The released PDGF is able to chemotactically recruit fibroblasts, monocytes, glia, and smooth muscle cells to migrate to the site of the wound. The released PDGF also acts as a mitogen by stimulating DNA synthesis in these cells, thereby increasing their proliferation rate. Quiescent SMC normally found in nonembryonic arterial walls, becomes synthetic and proliferative upon stimulation with the PDGF produced by endothelial cells, macrophages, and platelets. In this active state, SMC, themselves, produce PDGF AA which in turn, activates quiescent SMC.

It has been hypothesized that inhibiting the activity of PDGF may inhibit or reverse the formation of atherosclerotic plaques. To that end, a number of different molecules were tested as inhibitors or antagonists of PDGF. For example, fenofibrate (Kloer (1987) Am. J. Med. 83(B):3–8) and retinoic acid (Mordan (1989) Cancer Res. 49:906–909) inhibit PDGF-dependent stimulation of DNA synthesis. Monoclonal antibody C3.1 (Kawahara et al. (1987) Biochem. Biophys. Res. Commun. 147:839–845) and 5-methyl-7-diethylamino-s-triazolo (I,5-a) pyrimidine (Ohnishi et al. (1983) Life Sci. 31:2595–2602; Tiell et al. (1983) Artery 12:33–50) are PDGF antagonists. Interferon inhibits PDGF-induced protein synthesis in fibroblasts (Zagari et al. (1988) Biochem. Biophys. Res. Commun. 150:1207–1212) and inhibits the mitogenic effect of PDGF on fibroblasts (Hosang (1988) J. Cell. Physiol. 194:396–404). Suramin binds to PDGF and inhibits its biological activity (Hosang (1985) J. Cell. Biochem. 29:265–273), and protamine inhibits the binding of PDGF to its receptor (Huang (1984) J. Cell. Biol. 26:205–220).

The object of this invention is to inhibit the binding of PDGF to its receptors on responsive cells, and thus to inhibit the subsequent biological activities triggered by the binding of active PDGF to its receptors. It is also an object of the present invention to inhibit the formation of atherosclerotic lesions and fibrous plaques by inhibiting the biological activity of PDGF. Another object is to stop and/or to reverse the progression of atherosclerosis. Another object is to inhibit the proliferation of smooth muscle cells at the site of arterial injury or insult. Yet another object is to prevent the migration and proliferation of macrophages within the sub-intimal endothelial layer of mid- and large-sized muscular arteries.

SUMMARY OF THE INVENTION

This invention provides methods of antagonizing the activity of platelet derived growth factor (PDGF) with the use of polypeptides or antagonists having no PDGF-related biological activity, but having the ability to compete with biologically active forms of PDGF for PDGF receptors on cells. The polypeptides have an amino acid sequence sufficiently duplicative of at least a portion of an A chain of a biologically active form of PDGF such that it binds a cell membrane-bound receptor for native PDGF on a cell that responds biologically to the binding of PDGF. The binding of the polypeptide of the invention to a PDGF receptor effectively inhibits the binding of PDGF thereto, and in this way blocks the initiation of the biological activities triggered by PDGF binding. In some aspects of the invention, the polypeptide has at least 70% homology with residues 12–110 of the amino acid sequences for A chains of PDGF set forth in the sequence listing as SEQ ID NOS:1 and 3.

The polypeptide antagonists provided by this invention may be free of glycosylation and remain in monomeric form as they may be designed to lack the sulfhydryl group cross-linking sites prerequisite to form a biologically active PDGF dimer. In accordance with this aspect of the invention, the polypeptide may take the form of a cysteine-free or cysteine-blocked, full length or truncated A chain of PDGF such as an endothelial form of the A chain (see, e.g., SEQ ID NO:1) or a glioma form of the A chain (see, e.g., SEQ ID NO:3). Alternatively, the polypeptide may comprise a mutein, analog, or truncated analog of a PDGF A chain. Cysteine residues of the polypeptide may be blocked, for example, by conventional methods including sulfonation, pyridylethylation, or carboxymethylation.

Peptide fragments of a native A chain or analog or mutein thereof retaining have at least some residual specific affinity for a PDGF-specific receptor also are useful as PDGF antagonists. These fragments may assume a monomeric form because some or all of their Cys residues have been blocked or replaced with amino acids incapable of forming disulfide bonds. Alternatively, these fragments may be disulfide-bonded to a second polypeptide not having PDGF biological activity. Preferably, the fragment has an amino acid sequence homologous with a portion of a native endothelial or glioma species of a PDGF A chain, and more preferably, includes amino acid residue 80–110 or residues 12–41 thereof (see, e.g., SEQ ID NOS:1 and 3). One embodiment of the invention includes a C-terminal portion of an A chain.

The invention provides a DNA which, when transfected into a prokaryotic host such as *Escherichia coli* (*E. coli*), can be efficiently expressed as one of the polypeptides described above. The recombinant DNA includes a nucleotide sequence including a promoteroperator region operable in a prokaryote and a second nucleotide sequence encoding a polypeptide provided by the present invention. Also provided is a cell harboring and capable of expressing this DNA sequence.

Lastly, the invention provides a method of preparing these antagonist polypeptides including the steps of culturing a cell transfected with a DNA sequence encoding the polypeptide and capable of expressing it, and then purifying the synthesized polypeptide from the cell.

These and other features of the invention will be apparent from the description and claims which follow.

DESCRIPTION OF THE DRAWING

The foregoing and other objects of this invention, the various features thereof, as well as the invention itself, may be more fully understood from the following description, when read together with the accompanying drawing in which:

FIGS. 1A through 1G compare diagrammatic representations of various embodiments of the invention (FIGS. 1B–1G) with a highly diagrammatic representation of a disulfide-bonded, native PDGF dimer (FIG. 1A);

FIG. 2 is a schematic representation of a recombinant DNA of the invention comprising a structural gene encoding an endothelial A chain of PDGF, the corresponding amino acid sequence, and a restriction map;

FIG. 3 is a schematic representation of a recombinant DNA of the invention including a vector-derived polylinker region and a structural gene encoding a glioma A chain of PDGF, the corresponding amino acid sequence, and a restriction map; and FIG. 4 is a schematic representation of a recombinant DNA showing a Trp operator/promoter region, a structural gene encoding the modified LE leader peptide, and the corresponding amino acid sequence for the LE peptide. This operator/promoter - leader DNA is preferred for expressing the PDGF antagonists of FIGS. 1, 2, and 3 in *E. coli*.

DESCRIPTION OF THE INVENTION

PDGF elicits its biological activity by binding to particular cell surface receptors with high affinity. The binding to such a receptor by a PDGF dimer triggers a cascade of intracellular events which ultimately result in mitogenic, chemotactic, or other behavior of the cell on which the receptor is located. There are two known PDGF receptors: the "Type A" receptor binds the AA and BB homodimers of PDGF as well as the AB heterodimer; the "Type B" receptor binds the BB homodimer with high affinity and the AB heterodimer with low affinity. It is assumed that all cells sensitive to the various known species of PDGF include one or both of the PDGF receptor(s) and/or an as yet unrecognized receptor. For example, foreskin fibroblasts, which respond to AA, BB, and AB forms of PDGF, include both Type A and Type B receptors. SMC respond mitogenically to the AA homodimeric species of PDGF, and thus are hypothesized to have a Type A receptor. However, Type A receptor has not yet been isolated from SMC.

It has now been discovered that treatment of SMC and other PDGF-sensitive cells with A chain of PDGF that is incapable of PDGF biological activity inhibits the cascade of activities initiated by native PDGF. This PDGF antagonist binds to PDGF receptors, but does not initiate the intracellular events that induce a biological response by the cells having PDGF receptors. Because the receptor is bound by the PDGF antagonist, it is competitively inhibited or blocked from binding active forms of dimeric PDGF, and hence cannot initiate the characteristic PDGF response. This observation permits one to modulate the effect of PDGF in vitro and in vivo. Analogs or fragments of the A chain that are capable of receptor-binding also function in an inhibitory or antagonistic capacity, with the amount of inhibition being dependent on the binding constant of the fragment/receptor interaction. Monomeric forms of intact A chain and some truncated and dimeric forms bind avidly and can inhibit activity strongly.

FIGS. 1A through 1G compares the secondary structure of some embodiments of the invention with a highly schematized model of a native PDGF dimer. The dimer in FIG. 1A is depicted as two full-length chains connected by eight interchain disulfide bonds; however in the active form of the dimer, some of these disulfide bonds are intrachain linkages. As shown in FIG. 1B, an antagonist polypeptide of the invention may be a full-length A chain of PDGF obtained by separating purified native AA or AB dimer, and then reducing and blocking the Cys residues from redimerizing. Alternatively, the full length monomer may be a recombinantly produced protein whose Cys residues have been blocked after synthesis or replaced with a similarly charged, non-sulfur-containing amino acid such as serine. The antagonist may also take the form of a fragment of a full-length A chain monomer (FIG. 1C), or a dimeric fragment of a full-length A chain-containing dimer (FIG. 1D), or a partially blocked monomeric A chain which is disulfide-bonded to a second polypeptide not having PDGF biological activity (FIGS. 1E-1G), such as a fragment of an A or B chain.

Presently, several methods are known by which PDGF can be extracted from human platelets (Heldin et al., (1979) Proc. Natl. Acad. Sci. U.S.A. 76:3722-3726; Antoniades et al., (1979) Proc. Natl. Acad. Sci. U.S.A. 76:1809-1813). However, in addition to being expensive to perform, these methods are generally inefficient, yielding only up to about 5% of the original starting material. Improved recoveries have been obtained by following the procedure of Antoniades (U.S. Pat. No. 4,479,896) and Lipton et al. (U.S. Pat. No. 4,350,687), but yields are still limited by the availability of human platelets. Furthermore, the therapeutic use of products derived from human blood carries the risk of transmission of a number of diseases such as Acquired Immune Deficiency Syndrome.

A more efficient method of obtaining the polypeptide of the invention is to genetically engineer a host cell to express it from a transfected recombinant DNA. Eucaryotic proteins such as PDGF have been produced in eucaryotic cells such as yeast (EP Publication No. 0177957). However, because eucaryotes have the ability to modify a protein post-translationally, it often will still be necessary to reduce the resulting dimeric form, and then to block redimerization of the resulting monomeric product. Nevertheless, protein antagonists of the invention can be manufactured in eucaryotic cells if desired. If a dimeric fragment of a eucaryotically-produced PDGF dimer is desired as an antagonist, it can be obtained by cleaving the isolated dimer with the appropriate protease.

Because prokaryotes do not have the intracellular machinery to post-translationally modify their protein products, and because prokaryotes have a fast growth rate, are easy to manipulate, and are inexpensive to culture, they are the host cell of choice in the production of the inhibitor polypeptide of the invention. PDGF monomer obtained from prokaryotic hosts will not be glycosylated or folded into the dimeric conformation requisite for PDGF biological activity.

The processes for designing, manipulating, and recombining DNA which encode PDGF chains or any amino acid sequences of interest are generally well known in the art, and therefore, are not described in detail herein. Methods Of identifying and isolating genes encoding proteins of interest, or for constructing such genes, are well understood and developed. These processes are described in the patent and other literature (e.g., U.S. Pat. No. 4,431,739; Maniatis et al., *A Cloning Manual*, Cold Spring Harbor, 1984 et seq. and *Current Protocols in Molecular Biology*, Wiley Interscience Publishing, through the update preceding the filing of this application). In general, the methods involve selecting genetic material encoding amino acids which define the polypeptide of interest according to the genetic code.

Exemplary and currently preferred nucleic acid and amino acid sequences are known in the field (see, e.g., Bonthron et al. (1988) Proc. Natl. Acad. Sci. (USA) 85:1492-1496; Detscholtz et al. (1986) Nature 320:695-699). For example, there are at least two known human forms of the A chain; one is derived from endothelial cells (shown in the Sequence Listing as SEQ ID NO:1 and depicted schematically in FIG. 2), and a second longer species is derived from glioma cells (shown in the Sequence Listing as SEQ ID NO:3 and depicted schematically in FIG. 3).

The construction of DNAs encoding these and various other A chains of PDGF in addition to those disclosed herein, and other active PDGF A chain fragments, muteins, and analogs can be devised readily by those skilled in the art, and can be manufactured using known techniques. These techniques may involve the use of various restriction enzymes which make sequence specific cuts in DNA, DNA ligases which join deoxyribonucleic acid sequences, polymerases which catalyze the formation of new genetic material, probes for isolating PDGF-encoding sequences, and enzymatic addition of sticky ends to blunt-ended DNA.

One method for obtaining DNA encoding the polypeptides disclosed herein is by assembly of synthetic oligonucleotides produced in a conventional, automated, polynucleotide synthesizer, followed by ligation with appropriate enzymes, and conventional amplification. For example, overlapping, complementary DNA fragments comprising 15 bases may be synthesized semi-manually using phosphoramidite chemistry, with end segments left unphosphorylated to prevent polymerization during ligation. One end of the synthetic DNA is left with a "sticky end" corresponding to the site of action of a particular restriction endonuclease, and the other end is left with an end corresponding to the site of action of another restriction endonuclease.

Alternatively, this approach can be fully automated. The DNA encoding the A chain or fragment or analog thereof may be created by synthesizing longer single strand fragments (e.g., 50-100 nucleotides) in, for example, an oligonucleotide synthesizer (e.g., Biosearch), and then ligating the fragments. Alternatively, DNA encoding the polypeptide of interest may be synthesized from mRNA by reverse transcriptase, yielding a complementary DNA (cDNA) specific for that polypeptide. These methods for obtaining DNA are know, per se, and do not form a part of this invention.

The nucleotide sequence may encode an inhibitory analog or mutein of an A chain obtained by changing one or several amino acids of the sequences of FIGS. 2 or 3. For example, one or more Cys residues may be replaced with serine (Set) residues to reduce inter- and intrachain disulfide bonding. In addition, the nucleotide sequence may encode a truncated form or fragment of the A chain. Any number of changes in the nucleotide sequence encoding the amino acid sequence of a particular chain may be changed as long as the monomer can still bind to the PDGF receptor thereby to inhibit the mitogenic activity of a PDGF dimer. Experience with biologically active proteins derived from different species indicates that significant changes in amino acid sequences can be made while retaining inhibitory activity. Furthermore, several digestion fragments of full length PDGF A chain have been shown to inhibit PDGF activity (see TABLE 1), and these were produced by enzymatic cleavage with Endo Lys C, for example, which cleaves C-terminal to a Lys residue. It accordingly is apparent that the methods disclosed herein can be used to produce many different specific sequences which are active to antagonize PDGF.

Such constructs can be made using automated peptide synthesis techniques, but preferably are produced in a host cell by expression of recombinant DNA. The currently preferred protein production method involves fusion protein expression in prokaryotes followed by cleavage to produce mature product. Thus, a leader polypeptide, such as is depicted in FIG. 4, may be used to express such constructs in E. coli. Of course, other leaders may be used, and may be required if a different prokaryotic cell type is used as an expression vehicle. The leader may further encode a Met residue, or other preferably unique amino acid or amino acid sequence recognizable by a cleavage agent, at its C-terminal end, which serves to link the leader peptide to the N-terminus of an A chain construct. This conventional approach provides a conveniently located site for action of a site-specific endopeptidase or, for Met residues, cyanogen bromide. In FIG. 4 this Met residue is encoded by nucleotides at positions 260-262.

The expression of these synthetic PDGF-encoding DNA molecules is achieved via the transformation of a prokaryotic host cell with a vector containing the DNA. A number of useful prokaryotic host cells are known and available, E. coli being the most preferred. Other prokaryotes that may be used include Bacillus. Conventional transfection techniques also are known to those skilled in the art, and are useful in the practice of this invention.

Various types of vectors may be used in the transfection such as plasmids and viruses including bacteriophages. These vectors contain various promoter/operator sequences and other regulatory DNA sequences which are known and available, and which are used in achieving expression. The vectors may exploit various marker genes which impart to a successfully transfected cell a detectable phenotypic property that can be used to identify which of the family of clones has successfully incorporated the recombinant DNA of the vector.

Thus, a prokaryotic host is transformed with a vector containing DNA encoding a PDGF A chain, analog, or a mutein thereof, linked to a leader peptide, e.g., of the type which enables the prokaryotic host to express and to retain intracellularly the eucaryotic translation product as a fusion protein. The fusion protein is translated from the transfected DNA and stored within the host cell. In E. coli, storage is accomplished as the protein aggregates as inclusion bodies. To obtain the PDGF antagonist from the fusion protein, the inclusion bodies are purified from harvested host cells using any known purification method. Such methods may include, for example, enzymatic and detergent lysis of the host cells. The fusion protein may then be cleaved to remove the extraneous leader peptide portion of the molecule. Removal of the leader peptide may be accomplished, for example, by cleavage with cyanogen bromide (CNBr) at a Met residue linking the leader peptide to the A chain polypeptide. Of course, as those skilled in the art will appreciate, many other cleavage site/cleavage agent pairs may be used. The released single chain or fragment can then be isolated by known procedures such as gel filtration, CM cellulose chromatography, or high pressure liquid chromatography (HPLC).

If necessary, the isolated polypeptide may be retained in its single chain form, or blocked from dimerizing to active form, by inhibiting the formation of intermolecular disulfide bonds among the eight (or less) cysteine residues of one PDGF chain (or fragment) and the cysteine residues of a second chain (or fragment). Pyridylethylation (see e.g., Lockridge et al. (1987) J. Biol. Chem. 262:12945-12952), sulfonation (see, e.g., Hoppe et al. (1989) Biochem. 28:2956-2960), and carboxymethylation (see, e.g., Welinder (1988) Anal. Biochem. 174:54-54), for example, will block disulfide bond formation and hence inhibit PDGF dimerization. This step may not be necessary if truncated analogs of A chain are employed which do not spontaneously form dimers, or which form dimers which bind to the PDGF receptor but fail to activate the cell.

Alternatively, the host cells may be transformed with genes encoding a mutein or analog form of PDGF (or fragment thereof) which have a reduced number of Cys residues such that dimerization does not occur so readily or does not occur at all.

Peptide fragments also may be formed from A chain monomers by digestion with endopeptidases such as Endo Lys C or Endo Arg C. Fragments which exhibit receptor-binding ability and thus comprise part of the binding domain of active PDGF may be used to inhibit PDGF activity. For example, residues 12-41 and 80-110 of a native PDGF A chain receptor are useful. Such peptide fragments also may be pyridylethylated, carboxymethylated or S-sulfonated to prevent dimerization.

If some or all of the Cys residues are retained and left unblocked, the polypeptide may be disulfide-linked to a second polypeptide. This second polypeptide may be any polypeptide or fragment thereof which does not interfere with the PDGF receptor binding ability of the polypeptide to which it is linked, and which does not have PDGF biological activity.

In order for the polypeptides so prepared to act as antagonists, they must have the prerequisite three-dimensional conformation for receptor binding. This conformation is most likely maintained by relatively weak, noncovalent hydrogen bonds, hydrophobic and charge interactions, and strong covalent bonds between sulfur atoms (disulfide bonds). Polypeptides produced in eucaryotes most likely have the correct three-dimensional conformation for binding the PDGF receptor as they have been post-translationally modified to at least include disulfide bonds (if Cys residues are present).

However, antagonists which have been recombinantly produced in prokaryotic hosts or those which have been biochemically synthesized must be treated to assume a conformation conducive to binding. Treatment may include simple exposure to a solution having physiologic characteristics (such as phyiologic saline or buffer) to enable hydrophobic and charge interactions and hydrogen bonding to occur. However, if some disulfide bonding is required, the antagonist must be exposed to a physiologically compatible substance that facilitates oxidation of sulfhydryl group-containing amino acid residues. An exemplary substance with this ability is glutathione present in both reduced and oxidized forms. One useful method includes exposure of the antagonist to oxidized and reduced species of glutathione present at a 1:10 ratio and in a solution having a pH of between 7 and 8. This methodology is described in detail in copending patent application Ser. No. 155,066, entitled "Production of Platelet Derived Growth Factor (PDGF) and Muteins Thereof", filed Feb. 11, 1988, the specification of which is herein incorporate by reference.

Once the antagonists are prepared and allowed to assume a three-dimensional conformation conducive for receptor binding, they are tested for their ability to inhibit PDGF-induced biological activity in a cell having PDGF receptors. One method includes the determination of $^3$H-thymidine incorporation in a cell which normally is induced to proliferate in the presence of PDGF, but which simultaneously is exposed to the prospective antagonist and to biologically active PDGF. Antagonists of the invention reduce or inhibit the incorporation of radioactivity by competitively binding to a PDGF receptor, and hence by not initiating DNA synthesis. Polypeptides incapable of competitively binding to a PDGF receptor, or incapable of binding to such a receptor without initiating proliferation are not antagonists as defined herein. Thus, this simple test can be used to easily check the efficacy of any embodiment of the invention.

The following examples more fully illustrates preferred features of the invention, but are not intended to limit the invention in any way. All of the starting materials and reagents disclosed below are known to those skilled in the art, and are available commercially or can be prepared using well-known techniques.

EXAMPLES

1. Production of Polypeptide

PDGF A chain monomers were produced by recombinant means in *E. coli* as described in related copending patent application Ser. No. 155,066 filed Feb. 11, 1988, herein incorporated as reference, and as described below.

A gene block encoding a PDGF chain produced either by reverse transcription of mRNA for PDGF, or by the enzymatic assembly of synthetic oligonucleotides is cloned into the pUC8 cloning vector, and plated with competent *E, coli* strain JM83 on LB agar containing 50 μg/ml Ampicillin at 50 μg/ml X-gal indicator dye substrate (Messing et al., Nucleic Acids Res. (1981) 9:309). The pUC8 plasmid without insert gives rise to blue colonies of JM83 cells, while pUC with gene insert produces white colonies. White colonies are picked into 5 ml LB broth culture medium containing 50 μg/ml Ampicillin, and incubated overnight in a rotary shaker incubator at 37° C.

Plasmid DNA is prepared from these cultures by the alkaline lysis procedure (Maniatis et al., *Molecular Cloning, a Laboratory Manual* (1982) Cold Spring Harbor Laboratory, pp. 88-91). The DNA is analyzed by restriction digestion with suitable enzymes, followed by polyacrylamide gel electrophoresis (PAGE).

All synthetic genes are analyzed by dideoxy sequencing according to Sanger (J. Mol. Biol. (1975) 94:441). A given gene insert is isolated by restriction digestion followed by PAGE on 5% gels. After electroelution of the DNA fragment from the gel, the fragment is cloned into the m13 RF (replicative form) vector, transformed into competent cells of the *E. coli* strain JM101, and plated in the presence of X-gal and IPTG. White plaques are picked, and the infected cells are grown up overnight in 2YT broth. M13 recombinant phages are then isolated from culture supernatants by precipitation with polyethylene glycol. Single stranded phage DNA template for sequencing is prepared by phenol chloroform extraction.

The correct clones are retained for assembly with additional genes. DNA sequencing is performed on every assembly or modification step. DNAs encoding A chains produced in accordance with the foregoing methods are set forth in FIGS. 2 and 3 of the drawing.

The gene is taken from the pUC cloning vector and inserted, along with a synthetic TRP promoter/operator and downstream PDGF structural gene, into an expression vector derived from pBr322. This expression vector is then transfected into competent *E, coli* hosts which express the fusion protein and store it in inclusion bodies.

Cells are resuspended in 25 mM Tris, 10 mM EDTA, pH 8 (1 gram cells per 10 ml of buffer). Lysozyme is added to a final concentration of 0.1 mg/ml. The suspension is stirred for 30 min., sonicated, and centrifuged. The resulting pellet is resuspended in 25 mM Tris, 10 mM EDTA, pH 8 and 1% Triton X-100 (detergent), stirred for 1 hour, and centrifuged. The resulting pellet is then resuspended in 8M urea, 2.5 mM Tris, 1 mM EDTA, 10 mM DTT, pH 8. The solution is stirred for 30 minutes, centrifuged, and the supernatant is retained.

The remaining steps of the production procedure involve purification of the fused protein using ion exchange chromatography, cleavage with CNBr, purification of the PDGF chain using gel filtration, CM cellulose, and HPLC.

A CM cellulose column (2.5 ml of resin per gram of cells) is equilibrated in 6M urea, 2.5 mM ammonium acetate, 1 mM EDTA, 10 mM DTT, pH 6 (CM column buffer). The 8M urea supernatant is adjusted to pH 6 and loaded onto the column. The loaded column is then washed in CM column buffer. Protein bound to the column is eluted with a gradient of 0–0.3M NaCl in CM column buffer (333 ml per 10 ml resin). Column fractions are characterized on Laemlli 15% reducing-denaturing gels. The fractions which contain the cleanest fusion protein are pooled, dialyzed against water at pH 3, and lyophilized.

The fusion protein is resuspended in 5% formic acid at a particular concentration. CNBr is then added, and the solution is stirred at room temperature for 8–24 hours. After digestion the reaction solution is subjected to gel filtration through GF-05 Trisacryl in 0.1N acetic acid. The effluent is then lyophilized.

The digests are resuspended at 2 mg/ml in 6M urea, 2.5 mM ammonium acetate, 1 mM EDTA, 10 mM DTT, pH 6. The CM column (3 ml of resin per 10 mg of digest) is equilibrated in CM column buffer. The digest is loaded onto the column, washed in CM column buffer, and eluted with a gradient of 0–0.3M NaCl in CM column buffer (333 ml per 10 ml resin). Fractions which are determined to contain the PDGF monomer are then pooled.

Monomers are loaded onto a C18 column (J. T. Baker Inc., Phillipsburg, N.J.) and eluted using an acetonitrile/TFA gradient (25–55% $CH_3CN$ over 90 min). Fractions are characterized on Laemmli 15% reducing-denaturing gels. PDGF-containing fractions are pooled, and the acetonitrile is removed by rotary evaporation. The monomers are then lyophilized.

2. Prevention of Dimerization

The Cys residues of the monomeric PDGF A chain are pyridylethylated to prevent dimerization. Pure preparations of dimeric or oxidized PDGF AA are reduced in 50 mM Tris-HCl, 1 mM EDTA containing 6M urea and 28 mM DTT, pH 8.5, to a final concentration of about 1 mg/ml. The samples are incubated for 45 min, at 37° C., and then alkylated in 40 ξM 4-vinylpyridine at room temperature for another 45 min. The alkylation is terminated by dilution with 50 mM ammonium bicarbonate containing 2 mM EDTA, pH 8.5. The pyridylethylated PDGF A monomers are then purified by HPLC.

3. Production of Peptide Fragments

Peptide fragments of alkylated PDGF A monomers are prepared by cleavage with a lysine-specific endoproteinase Endo Lys-C. To a solution of monomeric (0.3 mg/ml) PDGF A is added urea to a final concentration of 1M. The pH is adjusted to 7.0 by the addition of 2M Trizma base. Endo Lys-C (Boehringer) is added at a ratio of 1/20 (w/w). Incubation is at 37° C. overnight.

The resulting peptides are purified by reversed-phase HPLC. The mixture is applied to a column (0.4×25 cm, Vydac 214 TP54) equilibrated in 0.1% aqueous trifluoroacetic acid. The column is washed with the same solvent until the UV absorbence at 220 nm reaches its initial value. Peptides are then eluted with a linear gradient from 15% acetonitrile in 0.1% aqueoustrifluoroacetic acid to 42% acetonitrile in 0.1% trifluoroacetic acid during 40 min. The flow rate is 0.7 ml/min. Fractions are collected for 1 minute each. The effluent is monitored by the UV absorbence at 220 nm.

Fractions are analyzed by SDS-polyacrylamide gel electrophoresis using a 13.5% gel containing 4M urea. The gels are stained with Coomassie Blue and/or silver nitrate. The fragments obtained are subsequently used for inhibition studies.

4. Inhibition Assay

Human foreskin fibroblasts are grown from explants of newborn foreskin. NIH/3T3 cells were obtained from S. Aaronson (NCI). Cells are cultured in Dulbecco's modified Eagle's medium (DMEM) supplemented with 10% fetal bovine serum at 37° C. in an atmosphere of 10% $CO_2$ and 90% air.

Cells are grown in 48-well plates to confluence and used for assay 3–4 days later. Different monomeric forms or fragments of PDGF monomers are added to the media, and after 18 hours 10 ξg PDGF AA dimer, AB dimer, or BB dimer and 2 ξCi/ml $^3$H-thymidine are added. The cells are incubated an additional 2 hours and washed at 4° C. three times with phosphate-buffered saline (PBS) and five times with 5% trichloroacetic acid (TCA). TCA-insoluble materials are solubilized in 0.1N NaOH/0.1% SDS. The amount of incorporated $^3$H-thymidine is determined with a Beckman liquid scintillation counter. Some representative results are shown in TABLE 1.

TABLE 1

| SAMPLE (A chain): | IDENTITY | HALF-MAX INHIBITION |
|---|---|---|
| A | Intact | 100 nM |
| A4 | aa 80–110 | 100 nM |
| A6 | aa 12–41 | >200 nM |

The A4 fragment is able to exert the same degree of inhibition of proliferation as the intact A chain. This result indicates that a PDGF receptor binding site may be included somewhere within the region defined by amino acid residues 80 through 110 at the C-terminus of the native A chain. However, fragment A6 also demonstrates some ability to inhibit proliferation, albeit to a lesser degree, a result which perhaps is indicative of a secondary binding domain near the N-terminus.

Furthermore, the full-length analog of the A chain has the ability to inhibit the proliferative effect of BB dimer, an unexpected result in view of the fact that the BB and AA dimers bind to different PDGF receptors. This result indicates that the A chain-related polypeptides of the invention can also bind to the BB receptor.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method of inhibiting binding of platelet-derived growth factor (PDGF) to a PDGF receptor on a cell surface, said method comprising the steps of:
    a) providing a biosynthetic polypeptide, incapable of PDGF activity, said polypeptide comprising an amino acid sequence selected from the group consisting of SEQ ID NO 2 and SEQ ID NO 4 wherein said polypeptide binds to the PDGF receptor; and
    b) contacting said cell with said polypeptide such that said polypeptide binds said receptor on said cell, wherein binding of said polypeptide to said receptor inhibits the binding of PDGF.

2. The method of claim 1, wherein said polypeptide comprises the amino acid sequence set forth in the Sequence Listing as SEQ ID NO:2.

3. The method of claim 1, wherein said polypeptide comprises the amino acid sequence set forth in the Sequence Listing as SEQ ID NO:4.

4. The method of claim 1 wherein said polypeptide comprises residues 12 through 110 of the amino acid sequences selcted from the group consisting of SEQ ID NO 2 and SEQ ID NO 4.

5. The method of claim 1 wherein said polypeptide comprises amino acid residues 12–41 of the Sequence Listing selected from the group consisting of SEQ ID NO:2 and SEQ ID NO:4.

6. The method of claim 1 wherein said polypeptide comprises amino acid residues 80–110 of the Sequence Listing selected from the group consisting of SEQ ID NO:2 and SEQ ID NO:4.

7. The method of claim 1 wherein said polypeptide is the product of expression of recombinant DNA in a prokaryotic host cell.

8. The method of claim 1 wherein said polypeptide is free of glycosylation.

9. The method of claim 1 wherein said polypeptide has an amino acid sequence comprising plural blocked cysteine residues.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 342 base pairs
( B ) TYPE: nucleic acid
( C ) STRANDEDNESS: single
( D ) TOPOLOGY: linear (  i  i  ) MOLECULE TYPE: synthetic DNA, protein (  i x  ) FEATURE:
    ( A ) NAME/KEY: CDS
    ( B ) LOCATION: 10..339
    ( D ) OTHER INFORMATION: /note="synthetic DNA encoding
        analogs of human platelet-derived PDGF, expressed
        in E. coli."

( x i ) SEQUENCE DESCRIPTION: SEQ ID NO:1:

```
GAATTCATG TCT ATC GAA GAA GCG GTA CCG GCT GTT TGT AAA ACT CGT            48
          Ser Ile Glu Glu Ala Val Pro Ala Val Cys Lys Thr Arg
           1           5                      10

ACT GTT ATC TAC GAA ATC CCG AGA TCT CAG GTT GAC CCG ACG TCT GCT          96
Thr Val Ile Tyr Glu Ile Pro Arg Ser Gln Val Asp Pro Thr Ser Ala
     15              20                  25

AAC TTC CTG ATC TGG CCA CCG TGT GTT GAA GTT AAA CGT TGT ACT GGT         144
Asn Phe Leu Ile Trp Pro Pro Cys Val Glu Val Lys Arg Cys Thr Gly
 30              35                  40                      45

TGT TGT AAC ACC TCG AGC GTT AAA TGT CAG CCG TCT CGT GTT CAC CAT         192
Cys Cys Asn Thr Ser Ser Val Lys Cys Gln Pro Ser Arg Val His His
             50              55                      60

CGA TCT GTT AAA GTC GCG AAA GTT GAA TAC GTT CGT AAG AAA CCG AAA         240
Arg Ser Val Lys Val Ala Lys Val Glu Tyr Val Arg Lys Lys Pro Lys
             65              70                  75

CTT AAG GAA GTT CAG GTT CGT CTG GAA GAA CAC CTG GAA TGT GCA TGC         288
Leu Lys Glu Val Gln Val Arg Leu Glu Glu His Leu Glu Cys Ala Cys
         80                  85                  90

GCT ACT ACA AGC TTG AAT CCG GAC TAC CGT GAG GAG GAC ACT GAC GTC         336
Ala Thr Thr Ser Leu Asn Pro Asp Tyr Arg Glu Glu Asp Thr Asp Val
         95                 100                 105

CGT TAA                                                                  342
Arg
110
```

( 2 ) INFORMATION FOR SEQ ID NO:2:

( i ) SEQUENCE CHARACTERISTICS:
        ( A ) LENGTH: 110 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ser Ile Glu Glu Ala Val Pro Ala Val Cys Lys Thr Arg Thr Val Ile
 1               5                  10                  15

Tyr Glu Ile Pro Arg Ser Gln Val Asp Pro Thr Ser Ala Asn Phe Leu
             20                  25                  30

Ile Trp Pro Pro Cys Val Glu Val Lys Arg Cys Thr Gly Cys Cys Asn
         35                  40                  45

Thr Ser Ser Val Lys Cys Gln Pro Ser Arg Val His His Arg Ser Val
     50                  55                  60

Lys Val Ala Lys Val Glu Tyr Val Arg Lys Lys Pro Lys Leu Lys Glu
 65                  70                  75                  80

Val Gln Val Arg Leu Glu Glu His Leu Glu Cys Ala Cys Ala Thr Thr
                 85                  90                  95

Ser Leu Asn Pro Asp Tyr Arg Glu Glu Asp Thr Asp Val Arg
             100                 105                 110
```

( 2 ) INFORMATION FOR SEQ ID NO:3:

( i ) SEQUENCE CHARACTERISTICS:
        ( A ) LENGTH: 404 base pairs ( B ) TYPE: nucleic acid
( C ) STRANDEDNESS: single
( D ) TOPOLOGY: linear ( i i ) MOLECULE TYPE: synthetic DNA, protein ( i x ) FEATURE:
( A ) NAME/KEY: CDS
( B ) LOCATION: 10..384
( D ) OTHER INFORMATION: /note="synthetic DNA encoding analogs of human platelet-derived PDGF, expressed in E. coli."

( x i ) SEQUENCE DESCRIPTION: SEQ ID NO:3:

```
GAATTCATG TCT ATC GAA GAA GCG GTA CCG GCT GTT TGT AAA ACT CGT        48
          Ser Ile Glu Glu Ala Val Pro Ala Val Cys Lys Thr Arg
          1               5                   10

ACT GTT ATC TAC GAA ATC CCG AGA TCT CAG GTT GAC CCG ACG TCT GCT      96
Thr Val Ile Tyr Glu Ile Pro Arg Ser Gln Val Asp Pro Thr Ser Ala
    15              20                  25

AAC TTC CTG ATC TGG CCA CCG TGT GTT GAA GTT AAA CGT TGT ACT GGT      144
Asn Phe Leu Ile Trp Pro Pro Cys Val Glu Val Lys Arg Cys Thr Gly
30                  35                  40                  45

TGT TGT AAC ACC TCG AGC GTT AAA TGT CAG CCG TCT CGT GTT CAC CAT      192
Cys Cys Asn Thr Ser Ser Val Lys Cys Gln Pro Ser Arg Val His His
            50                  55                  60

CGA TCT GTT AAA GTC GCG AAA GTT GAA TAC GTT CGT AAG AAA CCG AAA      240
Arg Ser Val Lys Val Ala Lys Val Glu Tyr Val Arg Lys Lys Pro Lys
                65                  70                  75

CTT AAG GAA GTT CAG GTT CGT CTG GAA GAA CAC CTG GAA TGT GCA TGC      288
Leu Lys Glu Val Gln Val Arg Leu Glu Glu His Leu Glu Cys Ala Cys
            80                  85                  90

GCT ACT ACA AGC TTG AAT CCG GAC TAC CGT GAG GAG GAC ACT GGT AGA      336
Ala Thr Thr Ser Leu Asn Pro Asp Tyr Arg Glu Glu Asp Thr Gly Arg
        95                  100                 105

CCG CGT GAA TCT GGT AAG AAA CGT AAG CGT AAA CGT CTG AAA CCG ACT      384
Pro Arg Glu Ser Gly Lys Lys Arg Lys Arg Lys Arg Leu Lys Pro Thr
110             115                 120                 125

TAAGGATCCG TCGACGTGCA                                                404
```

( 2 ) INFORMATION FOR SEQ ID NO:4:

( i ) SEQUENCE CHARACTERISTICS:
( A ) LENGTH: 125 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Ser Ile Glu Glu Ala Val Pro Ala Val Cys Lys Thr Arg Thr Val Ile
1               5                   10                  15

Tyr Glu Ile Pro Arg Ser Gln Val Asp Pro Thr Ser Ala Asn Phe Leu
            20                  25                  30

Ile Trp Pro Pro Cys Val Glu Val Lys Arg Cys Thr Gly Cys Cys Asn
        35                  40                  45

Thr Ser Ser Val Lys Cys Gln Pro Ser Arg Val His His Arg Ser Val
    50                  55                  60

Lys Val Ala Lys Val Glu Tyr Val Arg Lys Lys Pro Lys Leu Lys Glu
65                  70                  75                  80

Val Gln Val Arg Leu Glu Glu His Leu Glu Cys Ala Cys Ala Thr Thr
                85                  90                  95

Ser Leu Asn Pro Asp Tyr Arg Glu Glu Asp Thr Gly Arg Pro Arg Glu
            100                 105                 110
```

```
Ser Gly Lys Lys Arg Lys Arg Lys Arg Leu Lys Pro Thr
        115             120             125
```

( 2 ) INFORMATION FOR SEQ ID NO:5:

( i ) SEQUENCE CHARACTERISTICS:
        ( A ) LENGTH: 264 base pairs
        ( B ) TYPE: nucleic acid
        ( C ) STRANDEDNESS: single
        ( D ) TOPOLOGY: linear ( i i ) MOLECULE TYPE: synthetic DNA, protein ( i x ) FEATURE:
        ( A ) NAME/KEY: CDS
        ( B ) LOCATION: 82..264

( x i ) SEQUENCE DESCRIPTION: SEQ ID NO:5:

```
AATATTCTGA AATGAGCTGT TGACAATTAA TCATCGAACT AGTTAACTAG TACGCAAGTT          60

CTCGTAAAAA GGGTATCGAC A ATG AAA GCA ATT TTC GTA CTG AAA GGT TCA          111
                       Met Lys Ala Ile Phe Val Leu Lys Gly Ser
                        1           5                      10

CTG GAC AGA GAT CTG GAC TCT CGT CTG GAT CTG GAC GTT CGT ACC GAC          159
Leu Asp Arg Asp Leu Asp Ser Arg Leu Asp Leu Asp Val Arg Thr Asp
                15              20              25

CAC AAA GAC CTG TCT GAT CAC CTG GTT CTG GTC GAC CTG GCT CGT AAC          207
His Lys Asp Leu Ser Asp His Leu Val Leu Val Asp Leu Ala Arg Asn
            30              35              40

GAC CTG GCT CGT ATC GTT ACT CCC GGG TCT CGT TAC GTT GCG GAT CTG          255
Asp Leu Ala Arg Ile Val Thr Pro Gly Ser Arg Tyr Val Ala Asp Leu
        45              50              55

GAA TTC ATG                                                              264
Glu Phe Met
    60
```

( 2 ) INFORMATION FOR SEQ ID NO:6:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Lys Ala Ile Phe Val Leu Lys Gly Ser Leu Asp Arg Asp Leu Asp
 1               5              10               15

Ser Arg Leu Asp Leu Asp Val Arg Thr Asp His Lys Asp Leu Ser Asp
             20              25              30

His Leu Val Leu Val Asp Leu Ala Arg Asn Asp Leu Ala Arg Ile Val
         35              40              45

Thr Pro Gly Ser Arg Tyr Val Ala Asp Leu Glu Phe Met
     50              55              60
```